United States Patent
Thorne

(10) Patent No.: US 7,847,072 B2
(45) Date of Patent: *Dec. 7, 2010

(54) RAPID ISOLATION OF OSTEOINDUCTIVE PROTEIN MIXTURES FROM MAMMALIAN BONE TISSUE

(75) Inventor: Kevin Thorne, Austin, TX (US)

(73) Assignee: Zimmer Orthobiologics, Inc., Austin, TX (US)

( * ) Notice: Subject to any disclaimer, the term of this patent is extended or adjusted under 35 U.S.C. 154(b) by 688 days.

This patent is subject to a terminal disclaimer.

(21) Appl. No.: 11/766,185

(22) Filed: Jun. 21, 2007

(65) Prior Publication Data

US 2007/0249815 A1    Oct. 25, 2007

Related U.S. Application Data

(63) Continuation of application No. 10/606,190, filed on Jun. 25, 2003, now Pat. No. 7,241,874.

(60) Provisional application No. 60/391,566, filed on Jun. 26, 2002.

(51) Int. Cl.
*C07K 14/51* (2006.01)
*C07K 14/435* (2006.01)
*C07K 1/14* (2006.01)
*C07K 1/34* (2006.01)
*A61K 35/32* (2006.01)

(52) U.S. Cl. .................. 530/840; 530/412; 514/21; 424/549

(58) Field of Classification Search ........................ None
See application file for complete search history.

(56) References Cited

U.S. PATENT DOCUMENTS

| | | | | |
|---|---|---|---|---|
| 3,458,397 A * | 7/1969 | Millonig et al. | .............. | 435/325 |
| 4,172,128 A | 10/1979 | Thiele et al. | | |
| 4,294,753 A * | 10/1981 | Urist | .......................... | 530/395 |
| 4,434,094 A | 2/1984 | Seyedin et al. | | |
| 4,455,256 A | 6/1984 | Urist | | |
| 4,529,590 A | 7/1985 | LeVeen et al. | | |
| 4,596,574 A | 6/1986 | Urist | | |
| 4,619,989 A | 10/1986 | Urist | | |
| 4,627,982 A | 12/1986 | Seyedin et al. | | |
| 4,699,788 A | 10/1987 | Catsimpoolas et al. | | |
| 4,743,259 A | 5/1988 | Bolander et al. | | |
| 4,774,228 A | 9/1988 | Seyedin et al. | | |
| 4,789,663 A | 12/1988 | Wallace et al. | | |
| 4,795,467 A | 1/1989 | Piez et al. | | |
| 4,804,744 A | 2/1989 | Sen | | |
| 4,863,732 A | 9/1989 | Nathan et al. | | |
| 4,874,746 A | 10/1989 | Antoniades et al. | ........... | 514/21 |
| 4,902,296 A | 2/1990 | Bolander et al. | | |
| 5,236,456 A | 8/1993 | O'Leary et al. | ............... | 623/16 |
| 5,256,644 A | 10/1993 | Antoniades et al. | ........... | 514/12 |
| 5,290,558 A | 3/1994 | O'Leary et al. | ............. | 424/422 |
| 5,290,763 A | 3/1994 | Poser et al. | | |
| 5,371,191 A * | 12/1994 | Poser et al. | ................. | 530/350 |
| 5,393,739 A | 2/1995 | Bentz et al. | .................... | 514/12 |
| 5,403,825 A * | 4/1995 | Lagarde et al. | ................ | 514/21 |
| 5,484,601 A | 1/1996 | O'Leary et al. | ............. | 424/422 |
| 5,516,532 A | 5/1996 | Atala et al. | ................. | 424/548 |
| 5,563,124 A | 10/1996 | Damien et al. | | |
| 5,830,859 A | 11/1998 | Schmidt | ....................... | 514/12 |
| 5,968,556 A | 10/1999 | Atala et al. | ................. | 424/548 |
| 6,118,043 A | 9/2000 | Nies et al. | ...................... | 623/16 |
| 6,120,760 A | 9/2000 | Hötten et al. | .............. | 424/85.1 |
| 6,180,605 B1 | 1/2001 | Chen et al. | .................... | 514/12 |
| 6,211,157 B1 | 4/2001 | Benedict et al. | | |
| 6,305,379 B1 | 10/2001 | Wolfinbarger, Jr. | .......... | 128/898 |
| 6,492,327 B2 | 12/2002 | Junker et al. | | |
| 6,534,095 B1 | 3/2003 | Moore-Smith et al. | ...... | 424/549 |
| 6,582,471 B1 | 6/2003 | Bittmann et al. | | |
| 7,087,577 B2 | 8/2006 | Benedict et al. | | |
| 7,241,874 B2 * | 7/2007 | Thorne | ....................... | 530/412 |
| 7,341,999 B2 | 3/2008 | Akella et al. | .................. | 514/21 |
| 7,622,562 B2 * | 11/2009 | Thorne et al. | ............... | 530/350 |
| 2001/0007023 A1 | 7/2001 | Lough, Jr. et al. | ........... | 530/841 |
| 2001/0041792 A1 | 11/2001 | Donda et al. | ................ | 530/399 |
| 2002/0173453 A1 | 11/2002 | Akella et al. | ................. | 514/12 |
| 2003/0176345 A1 | 9/2003 | Dawson | ....................... | 514/12 |
| 2004/0072322 A1 | 4/2004 | Thorne | ....................... | 435/226 |

(Continued)

FOREIGN PATENT DOCUMENTS

EP    0 243 179 B1    10/1992

(Continued)

OTHER PUBLICATIONS

Folkman, "Angiogenic Therapy fo the Human Heart," American Heart Association 97:628-629 (1998).

(Continued)

*Primary Examiner*—Vera Afremova
(74) *Attorney, Agent, or Firm*—Howrey LLP

(57) ABSTRACT

A method for purifying bone-derived osteogenic proteins including a demineralization process, a protein extraction process, a high molecular weight ultrafiltration process, a low molecular weight ultrafiltration process, and a recovery process. The high and low ultrafiltration processes preferably select proteins having a nominal molecular weight between approximately 8 kilodaltons and approximately 50 kilodaltons. Processes of the present invention may be used to recover osteogenic proteins from bone demineralization waste streams.

18 Claims, No Drawings

U.S. PATENT DOCUMENTS

| | | | |
|---|---|---|---|
| 2005/0064041 A1 | 3/2005 | O'Leary et al. | 424/549 |
| 2005/0096274 A1 | 5/2005 | Lough et al. | 514/12 |
| 2006/0057184 A1 | 3/2006 | Nycz et al. | 424/426 |
| 2006/0286157 A1 | 12/2006 | Akella et al. | 424/445 |
| 2007/0066525 A1 | 3/2007 | Lee et al. | 514/12 |

FOREIGN PATENT DOCUMENTS

| | | |
|---|---|---|
| WO | WO88/03409 | 5/1988 |
| WO | WO 92/18142 | 10/1992 |
| WO | WO01/66130 | 9/2001 |
| WO | WO02/00244 | 1/2002 |
| WO | WO02/47713 | 6/2002 |
| WO | WO2005/084701 | 9/2005 |
| WO | WO2006/093545 | 9/2006 |
| WO | WO2007/053850 | 5/2007 |

OTHER PUBLICATIONS

Shu-ting Li, "Biologic Biomaterials: Tissue-Derived Biomaterials (Collagen)," CRC Press Inc. pp. 627-647 (1995).

Mueller et al., "Myordardial angiogenesis induction with bone protein derived growth factors (animal experiment)," Swiss Med Wkly 131:23-25 (2001).

Nakaoka et al., "Inhibition of Rat Vascular Smooth Muscle Proliferation in Vitro and In Vivo by Bone Morphogenetic Protein-2," J. Clin. Invest. 100(11)2824-2832 (1997.

Nakashima et al., "The Novel Zinc Finger-Containing Transcription Factor Osterix is Required for Osteoblast Differentiation and Bone Formation," Cell 108:176-29 (2002).

Ogawa et al., "Purification of Transforming Growth Factors $\beta 1$ and $\beta 2$ from Bovine Bone and Cell Culture Assays," Methods in Enzymology 198:317-327 (1991).

Rodeo et al., "Use of Recombinant Human Bone Morphogenetic Protein-2 to Enhance Tendon Healing in a Bone Tunnel," The American Journal of Sports Medicine 27(4):476-489 (1999).

Schumacher et al., "Induction of Neoangiogenesis in Ischemic Myocardium by Human Growth Factors," Clinical Investigation and Reports 97:645-650 (1998).

Seyedin et al., "Purification and characterization of two cartilage-inducing factors from bovine demineralized bone," Proc. Natl. Acad. Sci 82:2267-2271 (1985).

Vukicevic, et al., "Osteogenic Protein-1 (Bone Morphogenetic Protein-7) Reduces Severity of Injury After IschemicAcute Renal Failure in Rat," Journal of Clinical Evaluation 102(1):202-214 (1998).

Wolfinbarger, et al., "Demineralized Bone Matrix: Maximizing New Bone Formation for Successful Bone Implantation," Orthopedic Biology and Medicine: Musculoskeletal Tissue Regeneration, Biological Materials and Methods, pp. 93-117 (2002).

Yamashita, et al., "Growth/Differentiation Factor-5 induces Angiogenesis In Vivo," Experimental Cell Research 235:218-226 (1997).

* cited by examiner

RAPID ISOLATION OF OSTEOINDUCTIVE PROTEIN MIXTURES FROM MAMMALIAN BONE TISSUE

CROSS-REFERENCE TO RELATED APPLICATIONS

Pursuant to 35 U.S.C. §119(e) this application is a continuation of application Ser. No. 10/606,190, filed Jun. 25, 2003, which issued as U.S. Pat. No. 7,241,874 on Jul. 10, 2007, which claimed priority to U.S. Provisional Patent Application Ser. No. 60/391,566, entitled "Rapid Isolation of Osteoinductive Protein Mixtures from Mammalian Bone," filed Jun. 26, 2002, in the name of Kevin Thorne and Scott Boden.

FIELD OF THE INVENTION

The present invention relates generally to methods for the rapid, high yield recovery and isolation of bone morphogenetic proteins (BMPs) and other tissue-inductive proteins from mammalian bone. In another aspect, the invention relates to protein mixtures recovered from bone demineralization waste streams. The invention also comprises protein mixtures produced according to the foregoing methods, and to implantable devices for osteoinductive repair of bone and tendon repair or reconstruction.

BACKGROUND OF THE INVENTION

Mammalian bone tissue comprises a number of proteins, including structural proteins such as collagen as well as osteogenic proteins that induce or promote bone growth. Recognition of the existence of osteogenic proteins in bone tissue has led to the discovery of a family of protein molecules known as the Bone Morphogenetic Proteins (BMPs). BMPs are members of the TGF-β superfamily of proteins, which includes additional proteins that provide tissue-inductive responses in vivo, including TGF-β1, TGF-β2, and TGF-β3. Structures for proteins designated BMP-1 through BMP-18 have been isolated and additional related proteins may be found. The unique inductive activity of the BMPs; along with their presence in bone tissue, suggests that they are involved in the regulation of bone repair processes and possibly in the normal maintenance of healthy bone tissue. There is a great need for such proteins for the induction and/or augmentation of bone growth following surgical bone repair or reconstruction procedures in human and animal patients.

Much research has been directed to producing, either by recombinant DNA techniques or by purification of naturally occurring proteins, specific osteoinductive proteins and protein mixtures. Protein mixtures having BMPs and other inductive proteins may be isolated from bone tissue according to known procedures. One of the earliest such procedures is disclosed in U.S. Pat. No. 4,294,753 to Urist, which provides a process for isolating bone proteins from bone tissue by demineralizing the bone tissue in acid. The demineralized collagen bone matrix is reduced to gelatin by adding a mineral salt. Osteoinductive BMPs are extracted from the gelatin using a solubilizing agent, such as guanidine hydrochloride and/or urea. The solubilized proteins are then purified by dialysis and several washing steps.

The processes disclosed in the '753 patent are also inherently wasteful. The demineralization step—the first step in the BMP isolation procedure—involves contacting the bone with hydrochloric acid to dissolve the mineral components of the bone and separate them from the protein components. The mineralized acid medium is discarded. Because BMPs are soluble in acids, a significant fraction of the BMPs are immediately lost at the beginning of processing.

The chemical reagents used to solubilize and extract the osteogenic proteins from the demineralized bone in the '753 procedures, i.e., guanidine hydrochloride (GuHCl) and urea, are cytotoxic. Consequently, the bone proteins must be subjected to extensive and time-consuming purification procedures to ensure that the BMPs obtained by the isolation procedures are free of cytotoxic agents and remain osteogenic when administered to the patient.

U.S. Pat. No. 4,619,989, also to Urist, discloses an improved process for isolating BMPs that involves additional dialysis purification steps beyond those disclosed in the '753 patent. Such steps increase still further the time required to isolate usable BMP mixtures. In addition, the additional purification steps further reduce protein yield and, worse still, may remove BMP fractions that are either osteogenic per se or have a synergistic effect with the remaining BMP proteins.

An improved method of isolating and purifying BMP-containing mixtures is described in U.S. Pat. Nos. 5,290,763 and 5,371,191. Both the '763 and '191 patents disclose a multistep process to provide highly purified BMP-containing mixtures. The process involves demineralization, protein extraction, high and low molecular weight ultrafiltration steps, an anion exchange process, a cation exchange process, and a reverse-phase HPLC process. Although the resulting BMP-containing mixture is highly osteogenic, the process is lengthy, requires expensive equipment, and has low yields.

To be effective as an osteogenic agent, BMPs must be delivered to a site within the body and retained in place for a period of weeks or months. The '753 patent discloses the co-precipitation of BMPs with a calcium salt, such as calcium carbonate, calcium silicate or calcium oxalate. An improved matrix material for release of BMPs is disclosed in U.S. Pat. No. 4,596,574, also to Urist. The disclosed matrix comprises biodegradable porous ceramic material, such as tricalcium phosphate. The BMPs may be deposited in the pores of the ceramic material by immersing the ceramic material in a solution containing the BMPs and lyophilizing the solution away. According to the '574 patent, the BMP-loaded ceramic resulted in substantial additional bone growth for a given dosage, and also lowered the required threshold dose for inducing bone growth.

Another BMP and carrier matrix product is provided in U.S. Pat. No. 5,563,124 to Damien et al. The '124 patent discloses a carrier comprising calcium carbonate, specifically aragonite, to which a BMP mixture, such as the mixtures disclosed in U.S. Pat. No. 5,290,763, is added. The BMPs may be added to the carrier by applying a solution of the BMPs to the aragonite carrier and then lyophilizing the solution. Alternatively, calcium carbonate particulates can be mixed with a matrix such as collagen, fibrin or alginate dispersion to form a composite, with the BMP solution added after drying the composite. In a still further embodiment, BMPs in solution may be added to a dispersion, which is then mixed with particulate calcium carbonate and dried.

There remains a need for BMP mixtures that may be easily, quickly and economically isolated from bone tissue in high yields, promote rapid osteoinduction when implanted in a human or animal patient, and that are amenable to combination with a wide variety of carriers.

It is an object of the present invention to provide a rapid, economical process for obtaining osteogenic BMP mixtures from mammalian bone tissue.

It is another object of the present invention to provide processes for recovering osteogenic BMPs from bone demineralization waste streams.

It is another object of the invention to provide a process for obtaining osteogenic BMP mixtures in high yields from mammalian bone tissue.

It is a still further object of the invention to provide a method of isolating osteogenic BMP mixtures from mammalian bone tissue that minimizes loss of BMPs from the bone tissue source.

It is a further object of the invention to provide a method of isolating osteogenic BMP mixtures from mammalian bone tissue that minimizes or avoids altogether the use of time-consuming dialysis procedures.

It is a further object of the invention to provide protein mixtures prepared by the foregoing processes.

It is a further object of the invention to provide implantable devices comprising a mixture of BMPs isolated from mammalian bone tissue.

SUMMARY OF THE INVENTION

In one embodiment, the present invention comprises an improved and simplified process for the rapid, high yield recovery and isolation of osteogenic BMPs from mammalian bone. In particular, the method comprises providing clean bone particles, demineralizing the particles in a demineralization medium to provide demineralized bone matrix (DBM) particles, extracting BMPs from the DBM particles with an extracting agent, removing undesired high and low molecular weight compounds, and purifying the BMPs to obtain the BMP mixtures either in a solvent or in a solid form.

It is believed that about 75% of the osteogenic proteins in bone tissue remain bound to the bone collagen during bone demineralization, and may subsequently be recovered by conventional extraction processes known in the art. The 25% of inductive proteins that are lost due to acid solubilization during bone demineralization constitutes a significant loss of osteogenic activity. Accordingly, in one aspect, the invention provides a method to additionally scavenge and isolate the BMPs from this acid waste fraction.

Demineralization yields an acidic solution of solubilized bone mineral and osteoinductive bone matrix proteins, and demineralized bone powder. Because of fundamental differences in solution and matrix chemistry, separate processing protocols are described to facilitate extraction and recovery of osteoinductive proteins from these matrices.

In a preferred embodiment, clean bone particles or fragments are demineralized with a suitable acid, preferably hydrochloric acid, at a low pH. Some BMPs maybe extracted from the bone tissue by the demineralizing solution. Accordingly, the acid supernatant comprising the extracted mineral components of the bone tissue also comprises BMPs and, in one embodiment of the invention, is further treated to recover osteogenic proteins therefrom. However, a separate protein extraction agent is also preferably employed to better extract the proteins from the demineralized bone particles after separation from the mineralized supernatant. In particular, BMPs are preferably extracted from the DBM particles using guanidine hydrochloride (GuHCl), although urea may also be used as a protein extraction agent.

The GuHCl extract solution is filtered or centrifuged to remove large particles, and preferably subjected to two ultrafiltration steps, preferably tangential flow filtration (TFF). In the first ultrafiltration step, high molecular weight compounds are removed in a High Molecular Weight Ultrafiltration (HMWU) step. An ultrafiltration membrane having a nominal molecular weight cut off (MWCO) of 50 kD is preferably employed, although larger nominal MWCO membranes (e.g., 60, 70, 80, 90, 100, 110, or 120 kD) may alternatively be used.

The retentate (larger particles) is discarded and the filtrate is subjected to a second ultrafiltration step to remove low molecular weight compounds in a Low Molecular Weight Ultrafiltration (LMWU) step. An ultrafiltration membrane preferably having a nominal MWCO of about 8 kD is preferred, although larger or smaller nominal MWCO membranes (e.g., 5 kD, 7 kD, 10 kD, 12 kD, or 15 kD) may be used.

The desired osteogenic BMPs are separated from the protein extraction agent by one or more filtration steps, preferably one or more diafiltration steps. Because removal of GuHCl is especially important, the BMPs are first diafiltered into urea. To remove urea and any traces of GuHCl, the BMPs are then diafiltered from urea into dilute HCl, preferably 10 mM HCl. Final purification of the BMP mixtures is preferably performed by one or more purification steps such as lyophilization or precipitation. The purified BMP mixture may be redissolved in a suitable carrier liquid, such as 10 mmol HCl, or may be recovered in solid form, e.g., lyophilization or filtration, before packaging.

In another embodiment, the invention comprises a method for purifying BMP from bone tissue comprising demineralizing bone particles by contacting the bone particles with an acidic demineralization medium, extracting BMPs from the demineralized bone particles with an extracting agent, removing compounds having a molecular weight greater than a desired upper molecular weight threshold (e.g., 50 kD) by a high molecular weight filtration step, removing compounds having a molecular weight below a desired lower molecular weight threshold (e.g., 8 kD) by a low molecular weight filtration step, and recovering BMPs from the filters. Optionally, additional purification steps such as lyophilization, resuspension and/or precipitation may be performed.

In another aspect, the present invention comprises methods for recovery of osteogenic BMPs from a bone demineralization waste stream. More particularly, the present invention comprises contacting bone particles with an acidic demineralization medium, separating the mineralized supernatant solution from the demineralized bone particles, removing at least a portion of the minerals from the mineralized supernatant solution to provide a protein supernatant solution, extracting BMPs by contacting the protein supernatant solution with a protein extraction agent, removing undesired high and low molecular weight compounds, purifying the BMPs, and recovering the BMPs either in a liquid solvent or in a solid form.

In a further embodiment, the invention comprises methods for recovering osteogenic BMPs from a bone demineralization medium. One such method comprises demineralizing bone particles in an acid medium, separating the demineralized bone particles from the mineral-containing acid supernatant, and recovering BMPs from the mineralized acid supernatant. The mineral-containing acid supernatant may be treated with a mineral precipitation agent to remove at least a portion of the mineral from the supernatant, providing a protein supernatant solution. The BMPs may be extracted from the protein supernatant with a protein extraction agent, and recovered from the extracted protein medium by removing undesired high and low molecular weight compounds, purifying the BMPs, and recovering the BMPs either in a liquid solvent or in a solid form.

In. another embodiment, the invention comprises an osteogenic implant device for promoting or augmenting bone growth. The device comprises BMP mixtures obtained by the rapid purification methods described herein, a collagen matrix, and an acidic calcium phosphate salt.

DETAILED DESCRIPTION OF THE INVENTION

In one embodiment of the present invention, the process for producing BMP mixtures comprises providing clean bone tissue particles, demineralizing the particles, extracting BMPs from the particles, removing high and low molecular weight components by ultrafiltration, and purifying the BMP mixture by diafiltration, lyophilization and/or precipitation.

The starting material for the present process is mammalian bone, preferably human bone. Bovine bone may also be used, however, because it is readily available at low cost. Cortical bone tissue is preferred, although cancellous bone can also be used. Human, cortical bone tissue obtained from bone banks is a preferred starting material because it has already been cleaned and ground according to established protocols, from a documented source, and may be obtained in particle size distributions that are amenable to BMP extraction. A preferred size distribution for the particles is about 1000 μm or less.

Alternatively, starting bone tissue may be obtained from mammalian bone obtained from, e.g., an abbatoir, by cleaning operations known in the art, such as removing all soft tissue and then grinding and further cleaning the bone. High-pressure washing is preferably employed to clean the bone tissue prior to grinding, and its use may minimize—and preferably eliminate altogether—subsequent soaking and flotation steps. U.S. Pat. No. 5,371,191, to Poser et al., which is hereby incorporated by reference herein in its entirety, discloses other cleaning methods for bovine bones suitable for use in the present invention. Typically, the bone is ground into successively finer particles and soaked in detergent solution to remove non-bone material. The bone is ground to particles less than 4 mm in size, preferably about 1000 μm or less. The ground bone particles are soaked in detergent solution between grinding, and rinsed in a flotation tank to remove soft tissue.

In a preferred embodiment, cleaned bone tissue is demineralized by soaking the particles in a suitable acid to dissolve its mineral content. Hydrochloric acid is preferred, although other acids such as formic acid can alternatively be used. A solution of dilute HCl, preferably in a range of from about 0.6N to about 4.0N, more preferably from about 1.0M to about 3.0M, most preferably 2.0 N, is effective to demineralized bone. It is preferred that the pH of the demineralizing solution be controlled during demineralization at from about 0.4 to about 5.0, preferably from about 0.4 to about 2.0, more preferably at about 1.5 to prevent collagen hydrolysis.

The bone minerals and proteins are less soluble in lower acid concentrations (i.e., higher pH. Accordingly, it is theorized that low acid concentrations (or higher pH) should correspond to higher solution volumes, lower viscosity in the mixture, and higher filtration rates for the filtration steps in the process. On the other hand, the lower solubility of the proteins in lower acid concentrations also should result in higher protein loss during filtration, associated with the adhesion of proteins to the filtration membranes. Higher acid concentrations (lower pH), conversely, should result in faster mineral solubilization and smaller working solution volumes, but higher viscosity and thus slower filtration rates.

The demineralization solution may be agitated with, e.g., a stirrer, and is preferably maintained at room temperature. Additives such as $CaCl_2$ or other salts can be used to enhance the solubility of the bone minerals if desired. Octyl alcohol or other defoaming agents may also be used to prevent excessive foaming during demineralization.

The bone is soaked in acid until the bone is essentially fully demineralized. X-ray analysis may be used to evaluate the extent of demineralization. Alternatively, standard procedures can be developed through experience to determine the amount of time required for demineralization. Typically, at least two hours is required, although additional time may be required for larger batches.

Prior art approaches, e.g., as described in U.S. Pat. Nos. 4,294,753 and 4,455,256, both of which are hereby incorporated by reference in their entirety, describe discarding the acidic demineralization solution by dialysis and washing steps. Similarly, the approach described in U.S. Pat. No. 5,371,191 also discloses discarding the HCl demineralization solution. It is believed that the high solubilty of BMPs in acid results in extensive and unnecessary loss of osteogenic proteins in prior art BMP isolation processes. Accordingly, in contrast to prior art approaches, the present invention contemplates recovery of BMPs from the mineral-containing HCl demineralization solution.

BMP recovery from the demineralization waste stream may be accomplished either by adding a protein extraction agent directly to the HCl-and-bone-tissue demineralization solution, or more preferably by separating the mineralized acid supernatant from the demineralized bone particles, removing at least a portion of the minerals (primarily calcium phosphate) from the mineralized supernatant solution, and adding a protein extraction agent to the supernatant to extract the BMPs. This medium, referred to as an extracted protein medium, may then purified by the same procedures as outlined herein for the extract medium for the DBM particles. Alternatively, the extracted protein medium may be combined with the extraction medium from the DBM particles at some point in the processing procedures, and all of the BMPs from the bone tissue may be recovered as a single stream.

BMPs are extracted from the DBM particles (and/or solubilized in the HCl demineralization supernatant) by adding a suitable extraction agent, preferably high purity GuHCl, although urea may be alternatively used. GuHCl is a preferred denaturant because it is ionic and therefore also functions well as a solubilizing agent for maintaining proteins in solution. Where GUHCl is employed, concentrations may range from 1M to 8.0M or to the solubility limits of the GuHCl. Preferred concentrations are from 2M to 8M, more preferably 4M. Lower concentrations allow less expensive extraction, as less GuHCl is used, but with slower solubilization of the BMPs and possibly lower bioactivity and/or yields.

Preferably the GuHCl extraction is performed at about body temperature (37EC), although lower temperatures may also be used. The temperature of the denaturant can increase during the extraction process. A 4.0 GuHCl, ph 7.0 solution is a preferred extraction solution. Optionally, a chaotrope can be added during extraction to improve solubility of extracted proteins. Suitable chaotropes include calcium chloride ($CaCl_2$), magnesium chloride ($MgCl_2$), and cesium chloride ($CeCl_2$). Usually, extraction continues until substantially all of the noncollagenous bone proteins have been removed from the demineralized bone. A typical extraction takes about 3 hours, although higher yields can be obtained by increasing the extraction time.

Following demineralization, BMPs and other osteogenic proteins in the demineralized bone extract solution are then separated by two ultrafiltration steps to remove proteins larger than a high molecular weight limit, preferably 50 kD, and smaller than a low molecular weight limit, preferably 8 kD. The filtration is preferably tangential flow filtration. TFF provides a rapid and efficient method for concentrating dissolved molecules, (i.e., proteins, peptides, nucleic acids, carbohydrates and other biomolecules), desalting or exchange solution buffers and gross separation/fractionation. TFF is routinely used on solution volumes ranging from 200 ml to hundreds of liters and is capable of concentration them to volumes as small as 10 ml in a short period of time. TFF allows much faster and more convenient concentration, desalting, and fractionation than conventional dialysis, the process uses membrane filter cassettes that can be used more than once and the process can be easily scaled. Simple control of materials, membrane surface area and filtration path length allow for direct translation of conditions established during pilot scale to process or commercial scale.

Returning to the ultrafiltration steps, the extract solution is preferably first subjected to a high molecular weight ultrafiltration step in which proteins larger than the high molecular weight limit are removed. The high molecular weight ultrafiltration step advantageously separates soluble osteogenic BMPs from high molecular weight collagens, and although the entire procedure is preferably conducted with sterile bone, instruments and reagents, the HMWU also eliminates any extraneous bacteria and other microorganisms to ensure a sterile product. Ultrafiltration steps having pore sizes smaller than most bacteria, e.g., 20 microns or less permit sterilization by filtration.

In a preferred embodiment, the HWMU step is performed in a Millipore Pellicon® Model tangential flow filtration (TFF) apparatus using a 50 kD nominal MWCO, polyether sulfone (PES) filter to minimize protein adhesion to the filter material. It is preferred to select a filter with relative low protein binding to the filter material itself. The ultrafiltration is preferably conducted at temperatures in the range of 2° C. to 50° C., preferably room temperature. Larger MWCO filters could be used, up to about 120 kD or even higher. A TFF apparatus is preferred because such systems are readily scalable to larger (i.e., commercial) batch sizes. The retentate (i.e., material having a MW greater than 50 kD) from the HMWU step is discarded. The HMWU permeate is then subjected to a LMWU step in which proteins smaller than a low molecular weight limit are removed. The LWMU step is preferably performed in a TFF apparatus using an 8 kD nominal MWCO, PES filter, or other. filter having low protein binding. Because of the small pore size of the filters in the LWMU step, it may be desirable to dialyze the filters or wash with HCl or another acid to assist in the passage of GuHCl through the filter.

Although an 8 kD MWCO filter is preferred, larger or smaller nominal MWCO filters could be used, ranging from 5 kD to 15 kD. The ultrafiltration is preferably conducted at room temperature (22° C.) although temperatures ranging from 2° C. to 50° C. (or even higher, so long as the proteins are not denatured) are permissible. The LWMU step yields a retentate with a mixture of proteins having molecular weights within a desired range.

The retentate from the LWMU step comprises a mixture of BMPs and other osteogenic and non-osteogenic proteins that may be implanted in a human or animal patient to promote bone growth. It is essential that the extraction agent be removed from the BMPs. GuHCl is removed by a diafiltration in a TFF apparatus into urea at 1.0M to 8.0M, preferably 6.0M. The urea is then removed by diafiltration into dilute HCl, preferably 10 mM. The proteins are then recovered by lyophilization, followed by precipitation with acetone, resuspension in HCl and lyophilization. Additional purification by washing and/or reprecipitation of the BMPs from the wash medium may be provided.

The BMPs may advantageously be stored in sterile containers either as an osteogenic solution or as a lyophilized solid. It is preferred to maintain the solution or solid either under vacuum or inert gas atmosphere such as e.g., nitrogen, hydrogen, helium, argon, or mixtures.

Where the BMPs are maintained in an osteogenic solution, the proteins may be used by adding the solution to a solid carrier such as collagen or bone chips, or by mixing the solution with a liquid or slurried carrier such as blood, plasma, or bone marrow aspirate.

Where the BMPs are maintained as a lyophilized solid, the proteins may be combined with another solid carrier, such as collagen, hydroxyapatite, or a composite device.

EXPERIMENTAL

Experiment 1

Demineralization of Bone Tissue

The following experimental protocol is one embodiment of the invention for isolating BMP mixtures. It has been used to isolate BMPs from human bone tissue that exhibit osteogenic activity in rats. Other mammalian sources, preferably bovine or porcine, may also be used. All operations are conducted with sterile reagents in sterile equipment. A batch size of 100 g starting mineralized bone tissue has been used, but in commercial operation the batch size would preferably be much larger.

One hundred grams of clean, sterile mineralized human bone particles of 1000 microns or less was obtained from a certified bone bank source. The mineralized human bone powder was defatted with water heated to 37° C. In a sterile container with continuous agitation, approximately 500 ml of sterile water was added to the bone powder. The solution was warmed to 37° C. for one hour, after which the bone powder was separated from the water by centrifugation (3000 rpm for 15 minutes). The procedure was repeated twice to ensure complete lipid removal. Other lipid removal techniques known in the art may also be used, including the use of organic solvents such as alcohol. Removing lipids from the bone powder is important for rapid and complete isolation of BMPs.

Following the defatting procedure, the bone powder was demineralized. In a sterile container with continuous magnetic stirring, approximately 500 ml of sterile 2 N HCl was added to the bone powder until the pH stabilized at 1.5. Higher concentrations of HCl (e.g., 3.0 to 5.0) may be used but are more likely to fragment collagen molecules in the bone tissue, thus increasing viscosity and filtration time. The demineralization was allowed to proceed for about three hours after stabilization of the pH.

As the initial HCl was added, the mineral content of the bone was solubilized, increasing the pH. Initially, the pH rose rapidly, requiring frequent addition of HCl (each minute or even more frequently for the first several minutes) during the first thirty minutes of the procedure. After about thirty minutes, the pH stabilized at 1.5 and further addition of acid was not required. Demineralization may take from 1-24 hours, more preferably from 2-10 hours, and even more preferably from about 3 to about 3 ½ hours.

When the demineralization was complete, the acid was separated from the bone collagen by centrifugation at 3000 rpm for 20 minutes. Other separation methods known in the art may also be used, however. The supernatant was decanted for further processing, as described more fully in Experiment 6 below. After demineralization, the remaining tissue comprises primarily demineralized bone collagen and osteogenic proteins, and is known as demineralized bone matrix (DBM). The DBM was washed with successive sterile water and/or phosphate buffered saline (PBS) rinses until the pH reached 7.0, indicating complete acid removal.

Each wash was conducted by suspending the DBM in about 250 ml of water or PBS per 100 g starting mineralized bone, stirring for about 20 minutes, and then separating the wash and DBM, preferably by centrifugation as described previously. The wash solution (i.e., water or PBS) was decanted after each wash. Some osteogenic proteins may be present in the wash supernatant, and the initial water washes may be saved and combined with the original acid supernatant from the demineralization step for later BMP recovery according to the protocol in Experiment 6 below. Typically only the first water wash supernatant is saved, if any.

Four water washings were performed on the DBM, which will nearly always be sufficient to remove all of the acid. The bone was also further rinsed twice with 20× concentration PBS (i.e., phosphate buffered saline having twenty times the standard phosphate buffer concentration) with magnetic stirring for about 30 minutes to raise the pH to 7.0. After rinsing with 20× PBS, the DBM was further rinsed with standard PBS. (i.e., 1× PBS), followed by two sterilize water rinses to remove the saline buffer. After rinsing was completed, the bone was frozen at −80 C. for 1-2 hours, and then lyophilized overnight (or longer). After lyophilization, the mass of the DBM was measured. Demineralized bone is typically about 40% of the starting mass of the mineralized bone.

The bone powder was demineralized in acid according to known procedures. The previously described procedure provides one acceptable protocol. However, persons of skill in the art will readily appreciate that alternate protocols may also be followed with similar, acceptable results. Except for saving the acid demineralization supernatant for BMP recovery, the foregoing demineralization procedures are known in the art and are not, per se, part of the invention.

Experiment 2

Extraction of BMPs from Demineralized Bone

After the demineralization, the DBM was extracted with filter-sterilized guanidine hydrochloride (GuHCl) to solubilize the BMPs. In particular, 500 ml of 4.0M GuHCl, pH 7.0, was added to the DBM per 100 g starting mineralized bone. The extraction was continued for 72 hours with constant agitation in an incubator at 37° C. However, extraction conditions are not critical and longer or shorter time periods and higher or lower temperatures can be used acceptably. A preferred range of extraction times is 24-96 hours. Lower temperatures, down to about 0° C. may be used so long as the reagents remain in the liquid state. Similarly, higher temperatures may be used, the upper limit being determined by the increased denaturation of some of the osteogenic proteins. For this reason, temperatures below 50° C. are preferred.

After the extraction was complete, the GuHCl and dissolved osteogenic proteins were separated from the extracted DBM by centrifugation at 3000 rpm for 20 minutes. The liquid supernatant was decanted for further processing. To ensure that all. osteogenic proteins were recovered, the extracted DBM was washed once with 100 ml of sterile water and centrifuged as before. The supernatant water and any additional osteogenic proteins therein were added to the decanted GuHCl extract. Extracted DBM, essentially pure bone collagen that has been depleted of its osteoinductive proteins, is known as demineralized and devitalized bone matrix ("DVBM"). The DVBM was frozen and lyophilized as described for the demineralized bone. DVBM may be used as a matrix component for delivery of osteoinductive proteins.

Experiment 3

High and Low Molecular Weight Ultrafiltration

The GuHCl extract, optionally including the water from the rinse step, was then filtered in a HMWU step to remove high molecular weight, non-osteogenic proteins such as collagen and large collagen fragments, preferably in a Millipore Pellicon XL TFF apparatus. The filters are preferably made of a material that does not bind proteins such as polyethersulfone (PES). A TFF apparatus with a 50 kD molecular weight cutoff (MWCO) filter was used to process the extract collected from Example 2, although higher MWCO filters such as 60, 70, 75, 100 kD or even higher may be used. The GuHCl extract was circulated until the retentate was concentrated by a factor of from about two to about 100, i.e., the retentate volume ranges from one-half to one-hundredth of the volume added to the TFF apparatus. In the present Example, the retentate was concentrated about ten-fold, i.e., the retentate was concentrated to about one-tenth of the volume added to the TFF apparatus. Thus, for a starting volume of about 500 ml GuHCl extract, the retentate was concentrated to 50 ml.

After the initial concentration step, the retentate was then filtered further to ensure that all of the lower molecular weight osteogenic proteins (i.e., proteins below 50 kD) were passed through the filter into the permeate. This was done by slowly adding GuHCl at a reduced concentration of 1.0 M to the system while holding the retentate volume constant at its concentrated volume. The additional GuHCl may be added at other reduced concentrations, and in amounts from one to 100 times the concentrated retentate volume, the optimum amount being determined by measuring the concentration of osteogenic protein in the filter permeate. When the concentration of protein is immeasurable or has reached an insignificant level, the addition of further GuHCl may be discontinued. In the present Example, sixty retentate volumes of 1.0 M GuHCl were slowly added to the concentrated retentate, again holding retentate volume constant. The collected TFF permeate from the HMWU step, which contained the extracted proteins in GuHCl at a concentration between 1.0M and 4.0M, was then passed through a low molecular weight TFF apparatus.

The desired proteins from the HMWU step permeate were separated from lower molecular weight compounds in a Low Molecular Weight Ultrafiltration (LMWU) step using a TFF apparatus with a filter having an 8 kD MWCO. Alternate embodiments are possible using different filter sizes, preferably in the range of from 2 kD-12 kD, more preferably 5-10 kD. It is preferred that the filter comprise non-protein-binding materials such as PES as already discussed. In contrast to the removal of high molecular weight compounds discussed above, in the removal of low molecular weight compounds the retentate, rather than the permeate, retains the desired proteins, which generally are in the range of 13-36 kD. Thus, low molecular weight compounds such as GuHCl pass through the 8 kD MWCO filter and the desired proteins are retained. In the present Example, the volume of the HMWU step permeate was about 3 liters. This volume was concentrated to 50 ml. Thus, the low molecular weight TFF step may concentrate the GuHCl by a factor of from about two to about 1000, in the present Example about sixty-fold.

Experiment 4

Removal of GuHCl and Urea

Because GuHCl is cytotoxic, removal of GuHCl from the osteogenic proteins is an important aspect of the present invention. This may be accomplished in the same TFF apparatus. as the low molecular weight filtration step by performing one, and more preferably two, diafiltration steps to the low molecular weight filtration retentate. In the present Experiment, the GuHCl was removed from the BMPs by diafiltration in the LMWU apparatus by slowly adding twenty retentate volumes (about 1 liter) of 6.0 M urea, holding the retentate volume constant at 50 ml. Depending upon the batch size used, from 1 to 100 retentate volumes may be added. Diafiltration with urea removes substantially all of the GuHCl.

The urea and trace amounts of GuHCl were removed from the BMPs by performing a second diafiltration in the same apparatus by gradually adding, at constant retentate volume, sixty retentate volumes of 10 mM HCl. Other dilute HCl concentrations, e.g., 0.1 to 1000 mM, may be used with success, and other acids may be substituted for HCl. Low concentrations of HCl are particularly advantageous in urea and GuHCl removal because the proteins are soluble in such solutions.

Where the above-described optional diafiltration with urea has been performed, the diafiltration step with dilute acid can be conducted as a second diafiltration step. Alternately, the HCl diafiltration may be performed directly on the concentrated low molecular weight TFF retentate, without a separate urea diafiltration. Depending upon batch size, the HCl diafiltration is preferably conducted with from 1-1000 retentate volumes of dilute HCl, more preferably 10-100 retentate volumes.

To ensure that no osteogenic proteins were lost, the system was flushed with an additional two retentate volumes (100 ml) of the 10 mM HCl to provide a final retentate of about 150 ml of HCl containing the dissolved osteogenic proteins.

Experiment 5

Further Purification by Lyophilization and Precipitation

The diafiltered proteins recovered in HCl were frozen and lyophilized to remove acid and water, thereby providing a solid product. The proteins were further purified to ensure complete removal of urea and GuHCl by precipitation in acetone. The acetone precipitation step may be considered optional. The lyophilized proteins were first redissolved in a small volume, e.g., 1-5 ml, of 10 mM HCl. Ten volumes of cold, pure acetone were added to the protein solution and the mixture was maintained for thirty minutes at −20° C. in an ice bath to precipitate the proteins. The mixture was then ultracentrifuged at 15,000 rpm for twenty minutes. The acetone was decanted, and the proteins were resolubilized in 10 mM HCl, frozen and lyophilized.

It will be appreciated that alternate means of final purification may be performed. In particular, it may be simpler and easier to conduct multiple diafiltrations to remove GuHCl and urea, or perform a more extensive second diafiltration using greater volumes (e.g., up to several hundred column volumes) of 10 mM HCl. All such embodiments are within the scope of the invention.

Experiment 6

Recovery of Proteins from Acid Demineralization Supernatant

In addition to the recovery of proteins from the DBM itself, BMPs may be recovered from the mineral-containing acid supernatant collected during the bone demineralization step. The mineralized supernatant comprises calcium and phosphate ions in solution with HCl, as well as the desired bone proteins. In the present Experiment, the recovery was performed by first removing at least a portion of the calcium ions by adding about 2.4 liters of 0.72M solution of sodium oxalate to the acid supernatant, precipitating calcium oxalate and buffering the pH of the acid supernatant to about 2.0. The precipitated calcium oxalate was removed by centrifugation (3000 rpm for 15 minutes). PBS (1× concentration) was then added to the solution in an amount sufficient to buffer the pH to 7.0. For about 500 ml of acid supernatant, about 800 ml of PBS was sufficient. The supernatant solution from which calcium has been removed is generally termed a protein supernatant solution.

Isolation of the BMPs from the buffered protein supernatant solution was then achieved by essentially the same processing steps as recited for the DBM itself, i.e., high and low molecular weight ultrafiltration, and additional purification steps. Specifically, a HMWU step in a TFF apparatus was first performed to remove large collagen molecules and fragments from the bone demineralization step. The solution was filtered until the retentate volume was reduced from about 3700 ml to 50 ml. The desired proteins were suspended in the permeate. To ensure that as much protein as possible passed into the permeate, 60 retentate volumes (about 3 liters) of GuHCl was gradually added to the TFF apparatus while maintaining constant retentate volume.

The permeate from the HMWU step was then subjected to a LMWU step substantially as already described in Experiment 3 for the demineralized bone fraction, and further purified as described in Experiments 4 and 5. To avoid duplicative processing, in some instances the buffer/acid supernatant permeate could be combined with the permeate from the demineralized bone fraction and the two fractions could be processed together for the LMWU step, diafiltration into urea and dilute HCl, recovery, lyophilization, acetone precipitation and acid resuspension and lyophilization.

While various embodiments of the present invention have been described in detail, it is apparent that modifications and adaptations of those embodiments will occur to those skilled in the .art. For example, .the osteoinductive factors .can be used in various applications such as treating periodontal diseases and in facial reconstruction, as well as in treating other bone and joint problems. However, it is to be expressly understood that such modifications and adaptations are within the spirit and scope of the present invention, as set forth in the following claims.

What is claimed is:

1. A process for obtaining osteogenic proteins from mammalian bone tissue comprising:
   i) contacting bone tissue with an acidic demineralization medium to provide demineralized bone tissue and a mineral-containing supernatant;
   ii) separating the mineral-containing supernatant from the demineralized bone tissue; and
   iii) recovering osteogenic proteins from the mineral-containing supernatant,
   wherein said recovering comprises removing at least part of the mineral component of the mineral-containing supernatant to provide a protein supernatant solution;

extracting osteogenic proteins from the protein supernatant solution by contacting the protein supernatant solution with a protein extraction agent to provide an extracted protein medium;

filtering the extracted protein medium in a first ultrafiltration step using a first ultrafiltration membrane having a nominal molecular weight cutoff corresponding to a high molecular weight limit to provide a permeate comprising a first osteogenic solution;

filtering the first osteogenic solution in a second ultrafiltration step using a second ultrafiltration membrane having a nominal molecular weight cutoff corresponding to a low molecular weight limit to provide a retentate comprising a second osteogenic solution; and purifying the osteogenic proteins in the second osteogenic solution, wherein the first or the second ultrafiltration step comprises tangential flow filtration.

2. The method of claim 1 wherein the protein extraction agent comprises guanidine hydrochloride.

3. The method of claim 2 wherein purifying comprises removing the guanidine hydrochloride by at least one diafiltration step in which the osteogenic proteins are diafiltered into a diafiltration medium that does not comprise guanidine hydrochloride.

4. The method of claim 3 wherein purifying further comprises at least one purification operation selected from the group consisting of lyophilization and precipitation.

5. The method of claim 2 wherein purifying comprises a first diafiltration step in which at least a portion of the guanidine hydrochloride is removed by diafiltering the osteogenic protein into a first diafiltration medium comprising urea, and a second diafiltration step in which at least a portion of the urea is removed by diafiltering the osteogenic protein into a second diafiltration medium comprising dilute hydrochloric acid.

6. The method of claim 5 wherein purifying further comprises lyophilizing the proteins from the second diafiltration medium to provide a solid osteogenic protein mixture.

7. The method of claim 1 wherein the mineral component is removed by contacting the mineral-containing supernatant with a precipitating agent.

8. The method of claim 7 wherein the precipitating agent comprises sodium oxalate.

9. The method of claim 1 wherein extracting includes addition of a chaotrope.

10. The method of claim 1 wherein the osteogenic proteins are extracted with a protein extraction agent.

11. The method of claim 10 wherein the protein extracting agent comprises guanidine hydrochloride or urea.

12. The method of claim 9 wherein recovering includes removing the protein extraction agent.

13. The method of claim 12 wherein removing comprises diafiltration.

14. The method of claim 1 wherein filtering comprises diafiltration.

15. The method of claim 1 wherein recovering comprises purifying the osteogenic proteins.

16. The method of claim 15 wherein purifying comprises lyophilizing, precipitating or resuspending.

17. The method of claim 1 wherein separating comprises centrifuging the mineral-containing supernatant and the demineralized bone tissue.

18. The method of claim 1 wherein the acidic demineralization medium comprises hydrochloric acid.

* * * * *